United States Patent [19]

Tschollar et al.

[11] Patent Number: 5,298,497
[45] Date of Patent: Mar. 29, 1994

[54] METHOD FOR PREVENTING ONSET OF HYPERTENSION EMPLOYING A CHOLESTEROL LOWERING DRUG

[75] Inventors: Werner Tschollar, Lawrenceville, N.J.; Cary S. Yonce, Newtown, Pa.; James L. Bergey, Lansdale, Pa.; James C. Kawano, Narberth, Pa.

[73] Assignee: E. R. Squibb & Sons, Inc., Princeton, N.J.

[21] Appl. No.: 891,243

[22] Filed: Jun. 1, 1992

Related U.S. Application Data

[63] Continuation of Ser. No. 524,269, May 15, 1990, abandoned.

[51] Int. Cl.$^5$ ............... A61K 31/675; A61K 31/40; A61K 31/35; A61K 31/21
[52] U.S. Cl. ............................ 514/91; 514/423; 514/460; 514/510
[58] Field of Search .................. 514/91, 426, 460, 510, 514/824, 423

[56] References Cited

U.S. PATENT DOCUMENTS 4,871,721 6/1989 Biller .................................. 514/102
4,924,024 5/1990 Biller .................................. 558/202

FOREIGN PATENT DOCUMENTS

0219782A2 4/1987 European Pat. Off. .

OTHER PUBLICATIONS

Rett et al., Postgrad. Med. J. (U.K.) 1986 62/Supp. 1 pp. 59–64.
Overturf et al., Athers Sclerosis 59:283–299, 1986.
Olefsky et al, "Insulin Action and Resistance in obesity and non-insulin dependent type II diabetes mellitus," Am. J. Physiol. 1982; 243:E15-330.
Stout, R. W., "Insulin and atheroma–an update," Lancet 1987, I:1077–1079.
Ferrannini et al, "Insulin resistance in essential hypertension," N. engl. J. Med. 1987, 217:350–357.
Modan et al, "Hyperinsulinemia–alink between glucose intolerance, obesity, hypertension, dyslipoproteinaemia, elevated serum uric acid and internal kation imbalance," Diab. Met. 1987, 13:375–380.
Skarfors et al, "Do antihypertensive drugs precipitate diabetes in predisposed man?" Br. Med. J. 1989, 298:1147-1152.
Pollare et al, "Insulin Resistance is a Characteristic Feature of Primary Hypertension Independent of Obesity," Metabolism, vol. 39, No. 2 (Feb.), 1990, pp. 167–174.
Pollare et al, "A comparison of the effects of Hydrochlorothiazide and Captopril on glucose and Lipid metabolism in Patients with Hypertension," New England Journal of Medicine, 321:868-873 Sep. 28, 1989.
Rett et al, "Angiotensin converting enzyme inhibitors in diabetes: Experimental and human experience," Postgrad. Med. J. (U.K.), 1986 62/Suppl. 1 (59–64).
Jauch et al, "Captopril enhances insulin responsiveness of forearm muscle tissue in non-insulin-dependent diabetes mellitus," Eur. J. Clin. Invest. (U.K.), 1987, 17/5 (448–454).
Edelman et al, "Hyperkalemia During Treatment with HMG CoA Reductase Inhibitor," N. Engl. J. Med. (320, No. 18, 1219–20, 1989).
Zorn et al, "Prevention of Arteriosclerotic Lesions with Calcium Antagonists or Captopril in Different Rat Hypertension Models," J. Cardiovasc. Pharmacol. vol. 12 (Suppl. 6), 1988.
Someya et al, "Suppressive Effect of Captopril on Platelet Aggregation in Essential Hypertension," J. Cardiovasc. Pharmacol. 6:840-843, 1984.

(List continued on next page.)

*Primary Examiner*—Frederick E. Waddell
*Assistant Examiner*—Kimberly Jordan
*Attorney, Agent, or Firm*—Burton Rodney

[57] ABSTRACT

A method is provided for preventing or reducing the risk of hypertension in normotensive patients having insulin resistance by administering a cholesterol lowering drug, such as pravastatin, alone or in combination with an ACE inhibitor, especially one containing a mercapto moiety, such as captopril or zofenopril.

15 Claims, No Drawings

OTHER PUBLICATIONS

Mizuno et al, "The effects of the angiotensin I-converting enzyme inhibitor, captopril, on serum lipoperoxides level and the renin-angiotensin-aldosterone and kallikrein-kinin systems in hypertensive patients," Nippon Naibunpi Gakkai Zasshi, Feb. 20, 1984.

Mizuno et al, "Acute effects of captopril on serum lipid peroxides level in hypertensive patients," Tohoku J. Exp. Med., May, 1984, 143(1) pp. 127-128.

Beisterfer et al, "Angiotensin II Induces Hypertrophy, not Hyperplasia, of Cultured Rat Aortic Smooth Muscle Cells," Circ. Res. 62:749-756, (1988).

Overturf et al, "Hypertension and Atherosclerosis in Cholesterol-Fed Rabbits Part 1, Mild, Two-Kidney, One-Clip Goldblatt Hypertension treated with Enalapril," Atherosclerosis, 59:283-299, 1986.

Cecil, Textbook of Medicine, 16 Ed., pp. 239-241, 1983.

McClard et al, "Novel Phosphonylphosphinyl (P-C-P-C-) Analogues of Biochemically Interesting diphosphates, Syntheses and Properties of P-C-P-C-Analogues of Isopentenyl Diphosphate and Dimethylallyl Diphosphate," J.A.C.S. 1987, 109, 5544-5545.

Biller et al, "Isoprenoid (Phosphinylmethyl)phosphonates as Inhibitors of Squalene Synthetase," Journal of Medicinal Chemistry, 1988, vol. 31, No. 10, pp. 1869-1871.

METHOD FOR PREVENTING ONSET OF HYPERTENSION EMPLOYING A CHOLESTEROL LOWERING DRUG

This is a continuation of application Ser. No. 524,269, filed May 15, 1990, now abandoned.

FIELD OF THE INVENTION

The present invention relates to a method for preventing onset of hypertension in a normotensive mammalian species with insulin resistance by administering a cholesterol-lowering drug, preferably, an HMG CoA reductase inhibitor, such as pravastatin alone or in combination with an ACE inhibitor, such as captopril or ceranapril.

BACKGROUND OF THE INVENTION

The role of insulin resistance and consecutive hyperinsulinemia in the pathogenesis of non-insulin dependent diabetes (NIDDM) and atherosclerosis is firmly established, Olefsky, J. M., et al, "Insulin Action and Resistance in obesity and non-insulin dependent type II diabetes mellitus," Am. J. Physiol. 1982; 243:E15-E30. Reaven, G. M., "Role of insulin resistance in human disease," Diabetes 1988; 37:1595-1607. Stout, R. W., "Insulin and atheroma—an update," Lancet 1987; 1077-1079. Recently the atherogenic risk of elevated insulin concentrations in prediabetic insulin resistant states like obesity, glucose intolerance, essential hypertension and—surprisingly—in "healthy" subjects with normal oral glucose tolerance has gained increasing interest, Ferrannini, E., et al, "Insulin resistance in essential hypertension," N. Engl. J. Med. 1987; 317:350-357. Standl, E., "Hyperinsulinamie -eine Ursache der Makroangiopathie?" Akt Endokr Stoffw 1989; 10:41-46 (Sonderheft). Stout, R. W., supra, Torlone E., et al, "Effects of captopril on insulin-mediated carbohydrate and lipid metabolism in subjects with NIDDM and hypertension, "Diabetes 1989; 38(Suppl. 2):88A. Hyperinsulinemia appears to be the earliest and strongest detectable risk factor for coronary heart disease, Eschwege, E., et al, "Coronary heart disease mortality in relation with diabetes, blood glucose and plasma insulin levels. The Paris Prospective Study, ten years later," Horm. Metab. Res. Suppl. 1985; 15:41-46. Modan, M., et al, "Hyperinsulinemia—a link between glucose intolerance, obesity, hypertension, dyslipoproteinaemia, elevated serum uric acid and internal kation imbalance," Diab. Met. 1987; 13:375-380, and as a recent prospective study showed, insulin resistant hypertensive subjects have a markedly elevated risk to develop NIDDM in addition to their already high atherogenic risk, Skarfors, E. T., et al, "Do anti-hypertensive drugs precipitate diabetes in predisposed man? " Br. Med. J. 1989; 298:1147-1152.

Pollare, T., et al, "Insulin Resistance is a Characteristic of Primary Hypertension Independent of Obesity," Metabolism, Vol. 38, No. 12 (December), 1989:pp 1-9 discloses that hypertension is associated with hyperinsulinemia independently of either obesity or glucose tolerance.

Pollare T., al al, "A comparison of the Effects of Hydrochlorothiazide and Captopril on Glucose and Lipid metabolism in Patients with Hypertension," New England Journal of Medicine, 321:888-873 (Sept. 28) 1989, disclose that captopril appears to have beneficial or no effects on glucose and lipid metabolism.

In a recent randomized multicenter study performed with general practitioners in West Germany, it was found that out of 243 treated essential hypertensive patients, only 35.9% had a normal oral glucose tolerance test, while 40.6% had impaired glucose tolerance (IGT) and 23.5% manifest NIDDM. The vast majority of patients observed was hyperinsulinemic, Rett, K., et al, "Metabolic effects of Metoprolol versus Captopril in essential hypertension," Dtsch. Med. Wschr. (in preparation). This suggests, that among hypertensive subjects, there might be an even higher number of patients with glucose intolerance as previously expected. These subjects are at risk of developing both coronary artery disease and diabetes.

There is evidence that ACE-inhibition (ACEI) is able to positively influence insulin resistance, Rett, K., et al, "Verbesserte Insulinwirkung durch ACE-Hemmung beim Type 2-Diabetiker," Dtsch. Med. Wschr. 1988; 243-249. Rett, K., et al, "Role of angiotensin-converting enzyme inhibitors in early anti-hypertensive treatment in non-insulin dependent diabetes mellitus," Postgrad Med. J. 1989a; 64(Suppl. 3):69-73. Torlone, E., et al, supra, Rett, K., et al, "Angiotensin converting enzyme inhibitors in diabetes: Experimental and human experience," Postgrad. Med. J. (U.K.), 1986 62/Suppl. 1 (59-64)), and glucose metabolism in NIDDM. (Jauch, K., et al, "Captopril enhances insulin responsiveness of forearm muscle tissue in non-insulin-dependent diabetes mellitus," Eur. J. Clin. Invest. (U.K.), 1987, 17/5 (448-454)).

Edelman, S. et al, N. Engl. J. Med. (320, No. 18, 1219-20, 1989), "Hyperkalemia During Treatment with HMG CoA Reductase Inhibitor," discloses a case where a patient received lovastatin (ls) for hyperlipidemia and whose hypertension was initially well controlled with lisinopril. "LS treatment was started when cholestyramine and niacin treatment was not successful. The patient developed myositis and hyperkalemia and recovered after emergency treatment and withdrawal of LS. He later resumed taking LS (without consultation) and again developed severe myositis and hyperkalemia. He recovered when LS was withdrawn. Care is cautioned when LS and lisinopril are given in combination to patients at risk of hyperkalemia."

European Patent Application 0219782 to Scholkens (Hoechst) discloses the treatment of atherosclerosis, thrombosis and/or peripheral vascular disease in mammals using an angiotensin converting enzyme (ACE) inhibitor or its physiologically tolerable salts. It further discloses that because ACE is predominantly localized in the luminal plasma membrane of the endothelial cell, ACE inhibitors can interfere in platelet-endothelium interaction. In addition, Scholkens discloses that ACE inhibition potentiates the action of bradykinin (a strong stimulator of prostacyclin release from endothelial cells) by inhibiting its degradation and ACE inhibitors, consequently, have an inhibitory effect on platelet aggregation.

Zorn, J. et al, "Prevention of Arteriosclerotic Lesions with Calcium Antagonists or Captopril in Different Rat Hypertension Models," J. Cardiovasc. Pharmacol. Vol. 12 (Suppl 6), 1988, discloses beneficial effects in mesenteric arteries atherosclerosis with captopril in spontaneous hypertensive Okamoto rats (SHRs), but not in salt-sensitive Dahl rats.

Someya, N. et al, "Suppressive Effect of Captopril on Platelet Aggregation in Essential Hypertension," J. Cardiovasc. Pharmacol. 6:840-843, 1984, discloses at page 840 that "hypertension is closely related to the genesis and progress of atherosclerosis," and that "platelet function plays an important role in atherosclerosis, with platelet dysfunction demonstrable in several vascular diseases. It has been reported that platelet aggregation is increased in hypertensives. . ." At page 842, it is indicated that the "data demonstrated the inhibition of platelet aggregation in vivo after administration of captopril to hypertensive subjects. . ." At page 843, it is indicated that "platelet aggregability is greater in hypertensives than in normotensives . . . platelet abnormalities may be a risk factor in atherosclerosis. . . . If captopril possesses an antiplate aggregability effect in addition to its hypotensive effect, it may be very useful for the prevention of atherosclerosis and thrombotic diseases associated with hypertension."

Mizuno, K. et al "The effects of the angiotensin I-converting enzyme inhibitor, captopril, on serum lipoperoxides level and the renin-angiotensin-aldosterone and kallikrein-kinin systems in hypertensive patients," Nippon Naibunpi Gakkai Zasshi, Feb. 20, 1984, discloses that captopril is a beneficial antihypertensive agent for preventing serum lipoperoxides concentration (LPX)-induced atherosclerosis in hypertensive patients.

Mizuno, K. et al "Acute effects of captopril on serum lipid peroxides level in hypertensive patients," Tohoku J. Exp. Med., May, 1984, 143(1) p. 127-8, suggests that inhibition of angiotensin-converting enzyme by captopril offers a possible therapeutic approach to the treatment of atherosclerosis complicated with hypertension.

The role of the renin-angiotensin system in atherosclerosis is not clear. Campbell-Boswell Robertson, Exp. and Mol. Pathol. 35:265 (1981) reported that angiotensin II stimulated proliferation of isolated human vascular smooth muscle cells while Geisterfer et al, Circ. Res. 62:749-756 (1988) showed no proliferation (but stimulation of growth) of isolated rat vascular smooth muscle cells.

Overturf, M. et al, Atherosclerosis, 59:383-399, 1986, discloses that studies with ACE inhibitors in cholesterol fed rabbits show no significant effects in the development of atherosclerosis.

Cecil, Textbook of Medicine, 16 Ed., pp 239 to 241, indicates at page 240 that blood pressure is an accelerator of atherosclerosis.

U.S. Pat. Nos. 4,046,889 and 4,105,776 to Ondetti et al disclose proline derivatives, including captopril, which are angiotensin converting enzyme (ACE) inhibitors useful for treating hypertension.

U.S. Pat. No. 4,337,201 to Petrillo discloses phosphinylalkanoyl substituted prolines, including fosinopril, which are ACE inhibitors useful for treating hypertension.

U.S. Pat. No. 4,374,829 discloses carboxyalkyl dipeptide derivatives, including enalapril, which are ACE inhibitors useful for treating hypertension.

U.S. Pat. No. 4,452,790 to Karanewsky et al discloses phosphonate substituted amino or imino acids and salts thereof and covers (S)-1-[6-amino-2-[[hydroxy(4-phenylbutyl)phosphinyl]-oxy]-1-oxohexyl]-L-proline (SQ 29,852, ceranapril). These compounds are ACE inhibitors useful in treating hypertension.

U.S. Pat. No. 4,316,906 to Ondetti et al discloses ether and thioether mercaptoacyl prolines which are ACE inhibitors useful in treating hypertension. This Ondetti et al patent covers zofenopril.

There are several different classes of compounds which have serum cholesterol lowering properties. Some of these compounds are inhibitors of the enzyme HMG CoA reductase which is essential in the production of cholesterol, such as mevastatin (disclosed in U.S. Pat. No. 3,983,140), lovastatin also referred to as mevinolin (disclosed in U.S. Pat. No. 4,231,938), pravastatin (disclosed in U.S. Pat. No. 4,346,227) and velostatin also referred to as synvinolin (disclosed in U.S. Pat. Nos. 4,448,784 and 4,450,171).

Other compounds which lower serum cholesterol may do so by an entirely different mechanism than the HMG CoA reductase inhibitors. For example, serum cholesterol may be lowered through the use of bile acid sequestrants such as cholestyramine, colestipol, DEAE-Sephadex and poly(diallylmethylamine) derivatives (such as disclosed in U.S. Pat. Nos. 4,759,923 and 4,027,009) or through the use of antihyperlipoproteinemics such as probucol and gemfibrozil which apparently lower serum "low density lipoproteins" (LDL) and/or converts LDL into high density lipoproteins (HDL).

U.S. Pat. No. 4,759,923 mentioned above discloses that poly(diallylmethylamine) derivatives which are bile salt sequestrants may be used in conjunction with drugs which reduce serum cholesterol by mechanisms other than sequestration, such as clofibrate, nicotinic acid, probucol, neomycin, p-aminosalicylic acid or mevinolin (also referred to as lovastatin).

Squalene synthetase is a microsomal enzyme which catalyzes the reductive dimerization of two molecules of farnesyl pyrophosphate (FPP) in the presence of nicotinamide adenine dinucleotide phosphate (reduced form) (NADPH) to form squalene (Poulter, C. D.; Rilling, H. C., in "Biosynthesis of Isoprenoid Compounds", Vol. I, Chapter 8, pp. 413-441, J. Wiley and Sons, 1981 and references therein). This enzyme is the first committed step of the de novo cholesterol biosynthetic pathway. The selective inhibition of this step should allow the essential pathways to isopentenyl tRNA, ubiquinone, and dolichol to proceed unimpeded. Squalene synthetase, along with HMG-CoA reductase has been shown to be down-regulated by receptor mediated LDL uptake (Faust, J. R.; Goldstein, J. L.; Brown, M. S. Proc. Nat. Acad. Sci. U.S.A., 1979, 76, 5018-5022), lending credence to the proposal that inhibiting squalene synthetase will lead to an up-regulation of LDL receptor levels, as has been demonstrated for HMG-CoA reductase, and thus ultimately should be useful for the treatment and prevention of hypercholesterolemia and atherosclerosis.

One approach to inhibitors of squalene synthetase is to design analogs of the substrate FPP. It is clear from the literature that the pyrophosphate moiety is essential for binding to the enzyme. However, such pyrophosphates are unsuitable as components of pharmacological agents due to their chemical and enzymatic lability towards allylic C-O cleavage, as well as their susceptibility to metabolism by phosphatases.

P. Ortiz de Montellano et al in *J. Med. Chem.*, 1977, 20, 243-249 describe the preparation of a series of substituted terpenoid pyrophosphates (Table A), and have shown these to be competitive inhibitors of the squalene synthetase enzyme. These substances retain the unstable allylic pyrophosphate moiety of FPP.

TABLE A

| No. | X | Y | Z |
|-----|-----|-----|-----|
| 1 | CH$_3$ | CH$_3$ | H |
| 2 | H | H | H |
| 3 | C$_2$H$_5$ | H | H |
| 4 | I | H | H |
| 5 | H | I | H |
| 6 | CH$_3$ | H | SCH$_3$ |

Corey and Volante, J. Am. Chem. Soc. 1976, 98, 1291-3, have prepared FPP analog A and presqualene pyrophosphate (PS-PP) analog B as inhibitors of squalene biosynthesis. (Presqualene pyrophosphate is an intermediate in the conversion of FPP to squalene). These inhibitors possess methylene groups in place of the allylic oxygen moiety of FPP and PSQ-PP, but still retain the chemically and enzymatically unstable pyrophosphate linkage.

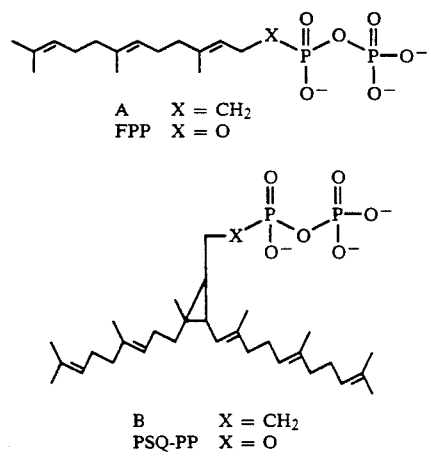

A    X = CH$_2$
FPP  X = O

B       X = CH$_2$
PSQ-PP  X = O

Poulter and co-workers have prepared cyclopropane C (Sandifer, R. M., et al., J. Am Chem. Soc. 1982, 104, 7376-8) which in the presence of inorganic pyrophosphate is an intermediate analog inhibitor of the enzyme squalene synthetase.

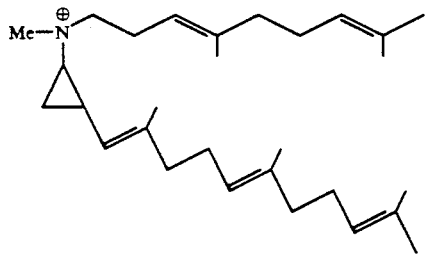

Altman and co-workers, Bertolino, A., et al., Biochim. Biophys. Acta. 1978, 530, 17-23, reported that farnesyl amine and related derivatives D inhibit squalene synthetase, but provide evidence that this inhibition is non-specific and probably related to membrane disruption.

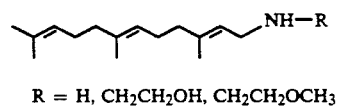

R = H, CH$_2$CH$_2$OH, CH$_2$CH$_2$OCH$_3$

Poulter, C. D., et al, J. Org. Chem., 1986, 51, 4768, prepared compound E in a demonstration of a synthetic method, but did not report any biological data.

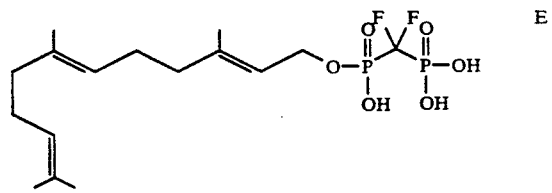

Poulter, C. D., Stremler, K. E., J.A.C.S., 1987, 109, 5542 describes the synthesis and biological evaluation of compounds having structure F. These compounds were evaluated as alternative substrates for avian liver farnesyl diphosphate and lemon peel cyclase.

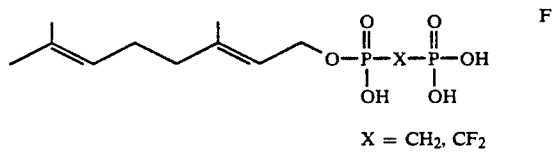

X = CH$_2$, CF$_2$

McClard, R. W., and Poulter, C. D., et al., J.A.C.S. 1987, 109, 5544, reported that phosphinylphosphonates G and H were competitive inhibitors of the 1'-4-condensation between isopentenyl diphosphate and geranyl diphosphate catalyzed by avian liver farnesyl diphosphate sunthetase. Phosphinylphosphonates G and H had Ki's of 19 μM and 71 μM, respectively. They also reported the speculative isolation of the farnesyl phosphinylphosphonate I, and the geranyl phosphinylphosphonate J from the enzymatic reaction of G with geranyl pyrophosphate or dimethylallyl pyrophosphate, respectively. The structures of I and J were tentatively assigned based on relative TLC mobilities. They hypothesized that I could be a potential inhibitor of squalene synthetase.

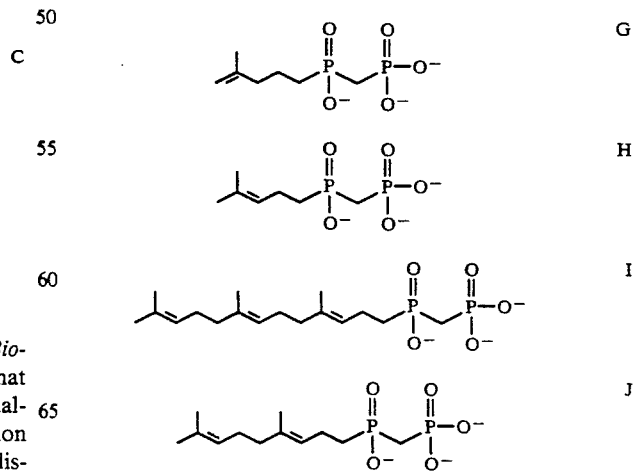

Capson, T. L., PhD dissertation, June 1987, Dept. of Medicinal Chemistry, the University of Utah, Abstract, Table of Contents, pp. 16, 17, 40–43, 48–51, Summary, discloses cyclopropanes of the structure discloses cyclopropanes of the structure

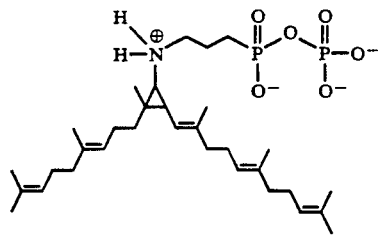

as intermediate analog inhibitors of squalene synthetase.

S. A. Biller et al., Journal of Medicinal Chemistry, 1988, Vol. 31, No. 10, pp 1869 to 1871 disclose that isoprenoid (phosphinylmethyl) phosphonates (PMPs) inhibit squalene synthetase. These phosphonates have the structures

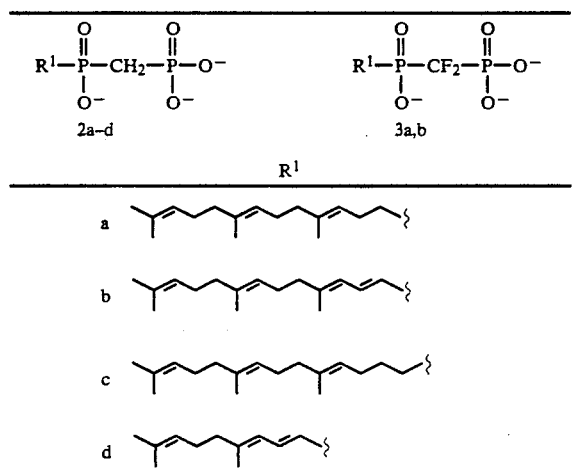

U.S. Pat. Nos. 4,871,721 and 4,924,024 disclose phosphorus-containing squalene synthetase inhibitors of the structure

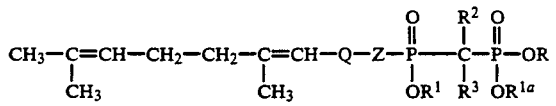

DESCRIPTION OF THE INVENTION

In accordance with the present invention, a method is provided for preventing onset or reduce risk of hypertension in normotensive mammalian species with insulin resistance, wherein a therapeutically effective amount of a cholesterol lowering drug, such as an HMG CoA reductase inhibitor alone or in combination with an angiotensin converting enzyme inhibitor is administered systemically, such as orally or parenterally.

The cholesterol lowering drug alone or with the ACE inhibitor will be administered to normotensive patients having insulin resistance or hyperinsulinemia in accordance with the method of the present invention.

The term "insulin resistance" or "hyperinsulinemia" as employed herein refers to a condition wherein higher than normal insulin concentrations are required to maintain normal glucose levels.

In preferred embodiments where the patient to be treated in accordance with the present invention is normotensive, the angiotensin converting enzyme inhibitor, where employed, will preferably be administered in amounts below that required to cause hemodynamic effects, that is below that required to cause a reduction in blood pressure.

The combination of the cholesterol lowering drug and ACE inhibitor will be employed in a weight ratio to each other of within the range of from about 0.001:1 to about 1000:1 and preferably from about 0.05:1 to about 100:1.

Cholesterol lowering drugs or drugs which are inhibitors of cholesterol biosynthesis which may be used in the method of the invention include HMG CoA reductase inhibitors, squalene synthetase inhibitors, fibric acid derivatives, bile acid sequestrants, probucol, niacin and the like.

The HMG CoA reductase inhibitors suitable for use herein include, but are not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, velostatin (synvinolin) and related compounds as disclosed in U.S. Pat. Nos. 4,448,784 and 4,450,171, with lovastatin, pravastatin or velostatin being preferred. Other HMG CoA reductase inhibitors which may be employed herein include, but are not limited to, fluindostatin (Sandoz XU-62-320), pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)alkyl]-pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-di-substituted pyrrole, furan and thiophene derivatives as disclosed in European Patent Application No. 0221025, naphthyl analogs of mevalonolactone as disclosed in U.S. Pat. No. 4,686,237, octahydro-naphthalenes such as disclosed in U.S. Pat. No. 4,499,289, keto analogs of mevinolin (lovastatin) as disclosed in European Patent Application No. 0,142,146 A2, as well as other known HMG CoA reductase inhibitors.

In addition, phosphinic acid compounds useful in inhibiting HMG CoA reductase suitable for use herein are disclosed in GB 2205837 which compounds have the moiety

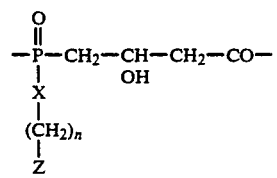

wherein X is —O— or —NH—, n is 1 or 2 and Z is a hydrophobic anchor.

Examples of such compounds include (S)-4-[[[4'-fluoro-3,3',5-trimethyl[1,1'-biphenyl]-2-yl-methoxy]methoxyphosphinyl]-3-hydroxy-butanoic acid, methyl ester or its monolithium salt, (S)-4-[[[4'-fluoro-3,3',5-trimethyl[1,1'-biphenyl]-2-yl]methoxy]hydroxyphosphinyl]-3-hydroxybutanoic acid, dilithium salt, (3S)-4-[[[4'-fluoro-3,3',5-trimethyl[1,1'-biphenyl]-2-yl]methoxy]methylphosphinyl]-3-hydroxybutanoic acid, monolithium salt, (S)-4-[[[2,4-dichloro-6-[(4-fluorophenyl)-methoxy]-phenylmethoxy]methoxyphosphinyl]-3-hydroxybutanoic acid, monolithium salt, (3S)-4-[[[2,4-dichloro-6-[(4-fluorophenyl)-methoxy]-phenyl]methoxy]hydroxyphosphinyl]-3-hydroxybutanoic acid, dilithium salt, (3S)-4-[[2,4-dichloro-6-[(4-fluorophenyl)-methoxy]-phenyl]methoxymethylphosphinyl]-3-hydroxybutanoic acid, or its methyl ester, and (S)-4-[[[4'-fluoro-3,3',5-trimethyl[1,1'-biphenyl-2-yl]methyl]amino]methoxyphosphinyl]-3-hydroxybutanoic acid, monolithium salt.

Another class of HMG CoA reductase inhibitors suitable for use herein include phosphinic acid compounds disclosed in GB 2205838, which compounds have the moiety

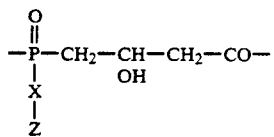

wherein X is —CH$_2$— —CH$_2$—CH$_2$—, —CH=CH—, —CH$_2$CH$_2$CH$_2$—, —C≡C— or —CH$_2$O—, where O is linked to Z, and Z is a hydrophobic anchor.

Examples of such compounds include (S)-4-[[[1-(4-fluorophenyl)-3-(1-methylethyl)-1H-indol-2-yl]ethynyl]hydroxyphosphinyl]-3-hydroxyfutanoic acid, or its sodium salt (SQ 33,600) (preferred) or its dilithium salt;

(S)-4-[[(E)-2-[4'-fluoro-3,3',5-trimethyl-[1,1'-biphenyl]-2-yl]ethenyl]hydroxyphosphinyl]-3-hydroxybutanoic acid or its dilithium salt;

(S)-4-[[2-[4'-fluoro-3,3',5-trimethyl-[1,1'-biphenyl]-2-yl]ethyl]hydroxyphosphinyl]-3-hydroxybutanoic acid, methyl ester or mono- or di-alkali metal salts thereof;

(S)-4-[[[4'-fluoro-3,3',5-trimethyl-[1,1'-biphenyl]-2-yl]ethynyl]methoxyphosphinyl]-3-hydroxybutanoic acid or the methyl ester thereof;

(5Z)-4-[[2-[4'-fluoro-3,3',5-trimethyl-[1,1'-biphenyl]-2-yl]ethenyl]hydroxyphosphinyl-3-hydroxybutanoic acid, methyl esters thereof;

(S)-4-[2-[3-(4-fluorophenyl)-1-(1-methyl-ethyl)-1H-indol-2-yl]ethylmethoxyphosphinyl]-3-hydroxybutanoic acid, methyl esters;

(S)-4-[[2-[1,1'-biphenyl-2-yl]ethyl]-methoxyphosphinyl-3-hydroxybutanoic acid, methyl ester;

(S)-4-[[2-[4'-fluoro-3,3',5-trimethyl-[1,1'-biphenyl]-2-yl]ethyl]hydroxyphosphinyl]-3-hydroxybutanoic acid, dilithium salt;

(S)-4-[[2-[4'-fluoro-3,3',5-trimethyl-[1,1'-biphenyl-2-yl]ethynylhydroxyphosphinyl]-3-hydroxybutanoic acid, dilithium salt;

(5Z)-4-[[2-[4'-fluoro-3,3',5-trimethyl-[1,1'-biphenyl]-2-yl]ethenyl]hydroxyphosphinyl]-3-hydroxybutanoic acid, dilithium salt;

(S)-4-[[2-[3-(4-fluorophenyl)-1-(1-methyl-ethyl)-1H-indol-2-yl]ethyl]hydroxyphosphinyl]-3-hydroxybutanoic acid, dilithium salt;

(S)-4-[[2-[(1,1'-biphenyl]-2-yl]ethyl]-hydroxyphosphinyl-3-butanoic acid, dilithium salt;

(S)-4-(hydroxymethoxyphosphinyl)-3-[[(1,1-dimethylethyl)diphenylsilyl]oxy]butanoic acid, methyl ester, or its dicyclohexylamine (1:1) salt;

(S)-4-[[2-[1-(4-fluorophenyl)-3-(1-methyl-ethyl)-1-indol-2-yl]ethynyl]hydroxyphosphinyl]-3-hydroxybutanoic acid or its dilithium salt or disodium salt or methyl ester thereof;

(E)-4-[[2-[3-(4-fluorophenyl)-1-(1-methyl-ethyl)-1H-indol-2-yl]ethenyl]hydroxyphosphinyl-3-hydroxybutanoic acid or its dilithium salt or methyl ester thereof;

4-[[2-[4'-fluoro-3,3',5-trimethyl[1,1'-biphenyl]-2-yl]ethylhydroxyphosphinyl]-3-hydroxy-butanoic acid or its dilithium salt or methyl ester thereof;

(E)-4-[2-[4'-fluoro-3,3',5-trimethyl[1,1'-biphenyl]-2-yl]ethenyl]hydroxyphosphinyl]-3-hydroxybutanoic acid or its dilithium salt or methyl ester thereof;

(S)-4-[[[2,4-dimethyl-6-[(4-fluorophenyl)-methoxy]-phenyl]ethyl]hydroxyphosphinyl]-3-hydroxybutanoic acid or its dilithium salt or methyl ester thereof;

(S)-4-[[[2,4-dimethyl-6-[(4-fluorophenyl)-methoxy]-phenylethynyl]hydroxyphosphinyl]-3-hydroxybutanoic acid or its dilithium salt or methyl ester thereof;

(S)-4-[[2-[3,5-dimethyl[1,1'-biphenyl]-2-yl]ethyl)hydroxyphosphinyl]-3-hydroxybutanoic acid or its dilithium salt or methyl ester thereof;

(S)-4-[[2-[4'-fluoro-3,5-dimethyl[1,1'-biphenyl]-2-yl]ethyl]hydroxyphosphinyl-3-hydroxybutanoic acid or its dilithium salt or methyl ester thereof;

(S)-4-[[2-[[1,1'-biphenyl]-2-yl]ethynyl]-hydroxyphosphinyl]-3-hydroxybutanoic acid or its dilithium salt or methyl ester thereof;

(S)-4-[[2-[5-(4-fluorophenyl)-3-(1-methyl-ethyl)-1-phenyl-1H-pyrazol-4-yl]ethynyl]methoxy-phosphinyl]-3-hydroxybutanoic acid, methyl ester;

(S)-4-[[2-[1-(4-fluorophenyl)-3-(1-methyl-ethyl)-1H-indol-2-yl]ethyl]hydroxyphosphinyl--hydroxybutanoic acid or its dilithium salt or methyl ester thereof;

(S)-4-[[2-[5-(4-fluorophenyl)-3-(1-methyl-ethyl)-1-phenyl-1H-pyrazol-4-yl]ethynyl]hydroxy-phosphinyl]-3-hydroxybutanoic acid, dilithium salt;

(E)-4-[[2-[5-(4-fluorophenyl)-3-(1-methyl-ethyl)-1-phenyl-1H-pyrazol-4-yl]ethenyl]methoxy-phosphinyl]-3-hydroxybutanoic acid, methyl ester;

(E)-4-[[2-[5-(4-fluorophenyl)-3-(1-methyl-ethyl)-1-phenyl-1H-pyrazol-4-yl]ethenyl]hydroxy-phosphinyl]-3-hydroxybutanoic acid, dilithium salt;

(S)-4-[[2-[5-(4-fluorophenyl)-3-(1-methyl-ethyl)-1-phenyl-1H-pyrazol-4-yl]ethyl]methoxy-phosphinyl]-3-hydroxybutanoic acid, methyl ester;

(S)-4-[[2-[5-(4-fluorophenyl)-3-(1-methyl-ethyl)-1-phenyl-1H-pyrazol-4-yl]ethyl]hydroxy-phosphinyl]-3-hydroxybutanoic acid, dilithium salt;

(S)-4-[[2-[3-(4-fluorophenyl)-5-(1-methyl-ethyl)-1-phenyl-1H-pyrazol-4-yl]ethyl]methoxy-phosphinyl]-3-hydroxybutanoic acid, methyl ester;

(S)-4-[[2-[3-(4-fluorophenyl)-5-(1-methyl-ethyl)-1-phenyl-1H-pyrazol-4-yl]ethyl]hydroxy-phosphinyl]-3-hydroxybutanoic acid, dilithium salt;

(S)-4-[[2-[3-(4-fluorophenyl)-5-(1-methyl-ethyl)-1-phenyl-1H-pyrazol-4-yl]ethynyl]methoxy-phosphinyl]-3-hydroxybutanoic acid, methyl ester;

(S)-4-[[2-[3-(4-fluorophenyl)-5-(1-methyl-ethyl)-1-phenyl-1H-pyrazol-4-yl]ethynyl]hydroxy-phosphinyl]-3-hydroxybutanoic acid, dilithium salt;

(S)-4-[[[4-(4-fluorophenyl)-1-(1-methyl-ethyl)-3-phenyl-1H-pyrazol-5-yl]ethynyl]methoxy-phosphinyl]-3-hydroxybutanoic acid, methyl ester;

(S)-4-[[[4-(4-fluorophenyl)-1-(1-methyl-ethyl)-3-phenyl-1H-pyrazol-5-yl]ethynyl]hydroxy-phosphinyl]-3-hydroxybutanoic acid, dilithium salt;

(S)-4-[[2-[4-(4-fluorophenyl)-1-(1-methyl-ethyl)-3-phenyl-1H-pyrazol-5-yl]ethyl]methoxy-phosphinyl]-3-hydroxybutanoic acid, methyl ester;

(S)-4-[[2-[4-(4-fluorophenyl)-1-(1-methyl-ethyl)-3-phenyl-1H-pyrazol-5-yl]ethyl]hydroxy-phosphinyl]-3-hydroxybutanoic acid, dilithium salt;

(S)-4-[[[1-(4-fluorophenyl)-4-(1-methyl-ethyl)-2-phenyl-1H-imidazole-5-yl]ethynyl]methoxy-phosphinyl]-3-hydroxybutanoic acid, methyl ester;

(S)-4-[[[1-(4-fluorophenyl)-4-(1-methyl-ethyl)-2-phenyl-1H-imidazol-5-yl]ethynyl]methoxy-phosphinyl]-3-hydroxybutanoic acid, methyl ester;

(S)-4-[[2-[1-(4-fluorophenyl)-4-(1-methyl-ethyl)-2-phenyl-1H-imidazol-5-yl]ethyl]methoxy-phosphinyl]-3-hydroxybutanoic acid, methyl ester;

(S)-4-[[2-[1-(4-fluorophenyl)-4-(1-methyl-ethyl)-2-phenyl-1H-imidazol-5-yl]ethyl]hydroxy-phosphinyl]-3-hydroxybutanoic acid, dilithium salt;

(S)-4-[[[2-(cyclohexylmethyl)-4,6-dimethyl-phenyl]ethynyl]hydroxyphosphinyl]-3-hydroxybutanoic acid or its dilithium salt or methyl ester thereof;

4-[[2-[2-(cyclohexylmethyl)-4,6-dimethyl-phenylethenyl]hydroxyphosphinyl]-3-hydroxybutanoic acid or its dilithium salt or methyl ester thereof;

(S)-4-[[2-[2-(cyclohexylmethyl)-4,6-dimethyl-phenylethyl]hydroxyphosphinyl]-3-hydroxybutanoic acid or its dilithium salt or methyl ester thereof;

4-[[[[4'-fluoro-3,3',5-trimethyl[1,1'-biphenyl]-2-yl]oxy]methyl]hydroxyphosphinyl]-3-hydroxybutanoic acid or its dilithium salt or methyl ester thereof;

4-[[[4'-fluoro-3,3',5-trimethyl[1,1'-biphenyl-2-yl]methyl]hydroxyphosphinyl]-3-hydroxy-butanoic acid or its dilithium salt or methyl ester thereof;

(S)-4-[[[1-(4-fluorophenyl)-3-methyl-2-naphthalenyl]ethynyl]hydroxyphosphinyl]-3-hydroxy-butanoic acid or its dilithium salt or methyl ester thereof;

(E)-4-[[2-[1-(4-fluorophenyl)-3-methyl-2-naphthalenyl]ethenylhydroxyphosphinyl]-3-hydroxybutanoic acid or its dilithium salt or methyl ester thereof;

(S)-4-[[2-[1-(4-fluorophenyl)-3-methyl-2-naphthalenyl]ethyl]hydroxyphosphinyl]-3-hydroxybutanoic acid or its dilithium salt or methyl ester thereof;

4-[[3-[4'-fluoro-3,3',5-trimethyl[1,1'-biphenyl-2-yl]propyl]methoxyphosphinyl]-3-hydroxybutanoic acid, methyl ester;

4-[[3-[4'-fluoro-3,3',5-trimethyl[1,1'-biphenyl-2-yl]propyl]hydroxyphosphinyl]-3-hydroxybutanoic acid, dilithium salt;

[1S-[1α(R*),2α,4αβ, 8β, 8αα]]-4-[[2-[8-(2,2-dimethyl-1-oxobutoxy)decahydro-2-methyl-1-naphthalenyl]ethyl]methoxyphosphinyl]-3-hydroxy-butanoic acid, methyl ester;

[1S-[1α(R*),2α,4αβ, 8β,8αβ]]-4-[[2-[8-(2,2-dimethyl-1-oxobutoxy)decahydro-2-methyl-1-naphthalenyl]ethyl]hydroxyphosphinyl]-3-hydroxy-butanoic acid, dilithium salt;

(S)-4-[[[3'-(4-fluorophenyl)spiro]cyclopentane-1,1'-[1H]indene]-2-yl]ethynyl]methoxyphosphinyl]-3-hydroxybutanoic acid, methyl ester; and (S)-4-[[[3'-(4-fluorophenyl)spiro]cyclopentane-1,1'-[1H]indene]-2-yl]ethynyl]hydroxyphosphinyl]-3-hydroxybutanoic acid, dilithium salt.

The squalene synthetase inhibitors suitable for use herein include, but are not limited to, those disclosed by Biller et al., supra, including isoprenoic (phosphinylmethyl)phosphonates such as those of the formula

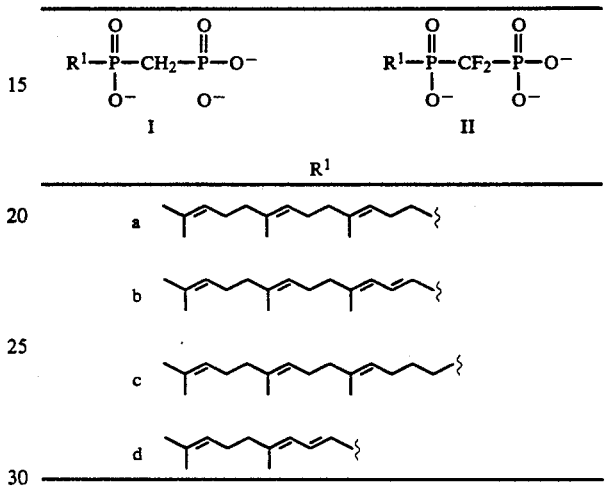

including the triacids thereof, triesters thereof and tripotassium and trisodium salts thereof as well as other squalene synthetase inhibitors disclosed in pending U.S. Pat. Nos. 4,871,721 and 4,924,024 and in Biller et al, J. Med. Chem., 1988, Vol. 31, No. 10, pp 1869 to 1871.

In addition, other squalene synthetase inhibitors suitable for use herein include the terpenoid pyrophosphates disclosed by P. Ortiz de Montellano et al., J. Med. Chem.; 1977, 20, 243–249, the farnesyl diphosphate analog A and presqualene pyrophosphate (PSQ-PP) analogs as disclosed by Corey and Volante, J. Am. Chem. Soc. 1976, 98, 1291–1293, phosphinylphosphonates reported by McClard, R. W. et al., J.A.C.S., 1987, 109, 5544 and cyclopropanes reported by Capson, T. L., PhD dissertation, June, 1987, Dept. Med. Chem. U. of Utah, Abstract, Table of Contents, pp. 16, 17, 40–43, 48–51, Summary.

Preferred are pravastatin, lovastatin or velostatin or a squalene synthetase inhibitor such as disclosed by Biller et al., supra or combinations thereof which include a weight ratio of the HMG CoA reductase inhibitor:squalene synthetase inhibitor of from about 0.05:1 to about 100:1.

Other cholesterol lowering drugs which function other than by inhibiting the enzyme HMG CoA reductase or squalene synthetase suitable for use herein include, but are not limited to, antihyperlipoproteinemic agents such as fibric acid derivatives, such as fenofibrate, gemfibrozil, clofibrate, bezafibrate ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex ®, Polidexide), as well as clofibrate, lipostabil (Rhone-Poulenc), Eisai E-5050 (an N-substituted ethanolamine derivative), imanixil (HOE-402) tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58–035, American Cyanamid CL-277,082 and CL-283,546 (di-substituted urea derivatives), nicotinic acid, neomycin, p-aminosalicylic acid, aspirin, poly-(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents which lower cholesterol through a mechanism other than by the inhibition of the enzyme HMG CoA reductase or squalene synthetase.

Also preferred are combinations of any of the HMG CoA reductase inhibitors, preferably pravastatin, or isoprenoid (phosphinylmethyl) phosphonates disclosed by Biller et al., supra, gemfibrozil or fenofibrate.

The angiotensin converting enzyme inhibitor which may be employed herein preferably includes those containing a mercapto (-S-) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril, that is

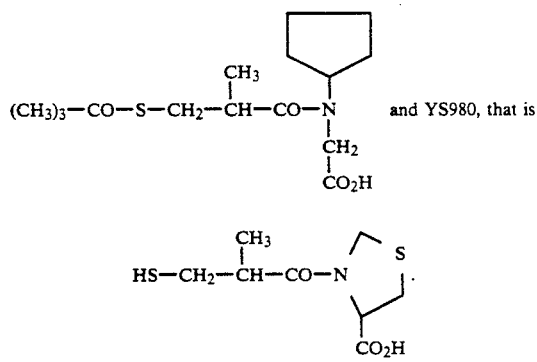

and YS980, that is

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)-phosphinyloxy]-1-oxohexyl]-L-proline (S 29,852 or ceranapril) being preferred, phosphinylalkanoyl prolines disclosed in U.S. Pat. No. 4,168,267 mentioned above with fonopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European patent Nos. 80822 and 60668; Chugai's MC-838 disclosed in CA. 102:72588v and Jap. J. Pharmacol. 40:373 (1986); Ciba-Geigy's CGS 14824 (3-(1-ethoxycarbonyl-3-phenyl-(1S)-propyl]-amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechst) disclosed in Eur. Patent No. 79-022 and Curr. Ther. Res. 40:74 (1986); Ru 44570 (Hoechst) disclosed in Arzneimittelforschung 35:1254 (1985), cilazapril (Hoffman-LaRoche) disclosed in J. Cardiovasc. Pharmacol. 9:39 (1987); $R_o$ 31-2201 (Hoffman-LaRoche) disclosed in FEBS Lett. 165:201 (1984); lisinopril (Merck) disclosed in Curr. Therap. Res. 37:342 (1985) and Eur. patent appl. No. 12-401, indalapril (delapril) disclosed in U.S. Pat. No. 4,385,051; indolapril (Schering) disclosed in J. Cardiovasc. Pharmacol. 5:643, 655 (1983); spirapril (Schering) disclosed in Acta. Pharmacol. Toxicol. 59 (Supp. 5):173 (1986); perindopril (Servier) disclosed in Eur. J. Clin. Pharmacol. 31:519 (1987); quinapril (Warner-Lambert) disclosed in U.S. Pat. No. 4,344,949 and CI 925 (Warner-Lambert) ([3S-[2[R(*)R(*)]]3R(*)]-2-[2-[[1-(ethoxycarbonyl)-3-phenylpropylamino-[-1-oxopropyl-1,2,3,4-tetrahydro-6,7-dimethoxy-3-isoquinolinecarboxylic acid HCl) disclosed in Pharmacologist 26:243, 266 (1984), WY-44221 (Wyeth) disclosed in J. Med. Chem. 26:394 (1983).

Preferred are those ACE inhibitors which are proline or substituted proline derivatives and most preferred are such ACE inhibitors which include a mercapto group.

The above-mentioned U.S. patents are incorporated herein by reference.

In carrying out the method of the present invention, the cholesterol lowering drug alone or in combination with the ACE inhibitor may be administered to mammalian species, such as monkeys, dogs, cats, rats, humans, etc., and as such may be incorporated in a conventional systemic dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid of sodium bisulfite) or the like. Oral dosage forms are preferred, although parenteral forms are quite satisfactory as well.

The dose administered must be carefully adjusted according to age, weight and condition of the patient, as well as the route of administration, dosage form and regimen and the desired result.

Thus, for oral administration, a satisfactory result may be obtained employing the HMG CoA reductase inhibitor in dosages employed, for example, for lovastatin as indicated in the Physician's Desk Reference, such as in an amount within the range of from about 1 to 2000 mg, and preferably from about 4 to about 200 mg. The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount of from about 0.1 to about 100 mg, preferably from about 5 to about 80 mg, and more preferably from about 10 to about 40 mg.

A preferred oral dosage form, such as tablets or capsules will contain the squalene synthetase inhibitor in an amount of from about 10 to about 500 mg, preferably from about 25 to about 200 mg.

The other serum cholesterol lowering drugs when present will be employed in dosages normally employed as indicated in the Physician's Desk Reference, for each of such agents such as in an amount within the range of from about 2 mg to about 7500 mg and preferably from about 2 mg to about 4000 mg.

With regard to the ACE inhibitor, for oral administration, a satisfactory result may be obtained employing the ACE inhibitor in an amount within the range of from about 0.01 mg/kg to about 100 mg/kg and preferably from about 0.1 mg/kg to about 5 mg/kg.

A preferred oral dosage form, such as tablets or capsules, will contain the ACE inhibitor in an amount of from about 0.1 to about 500 mg, preferably from about 2 to about 5 mg, and more preferably from about 1 to about 3 mg.

For parenteral administration, the ACE inhibitor will be employed in an amount within the range of from about 0.005 mg/kg to about 10 mg/kg and preferably from about 0.005 mg/kg to about 0.3 mg/kg.

The cholesterol lowering agent and ACE inhibitor may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

Tablets of various sizes can be prepared, e.g., of about 2 to 2000 mg in total weight, containing one or both of the active substances in the ranges described above, with the remainder being a physiologically acceptable carrier of other materials according to accepted pharmaceutical practice. These tablets can, of course, be scored to provide for fractional doses. Gelatin capsules can be similarly formulated.

Liquid formulations can also be prepared by dissolving or suspending one or the combination of active substances in a conventional liquid vehicle acceptable for pharmaceutical administration so as to provide the desired dosage in one to four teaspoonsful.

Such dosage forms can be administered to the patient on a regimen of one to four doses per day.

According to another modification, in order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

Fixed combinations of cholesterol lowering drug and ACE inhibitor are more convenient and are preferred, especially in tablet or capsule form for oral administration.

In formulating the compositions, the active substances, in the amounts described above, are compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, aspartame, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

Some of the active substances described: above form commonly known, pharmaceutically acceptable salts such as alkali metal and other common basic salts or acid addition salts, etc. References to the base substances are therefore intended to include those common salts known to be substantially equivalent to the parent compound.

The formulations as described above will be administered for a prolonged period, that is, for as long as the potential for hypertension or insulin resistance remains or the symptoms continue. Sustained release forms of such formulations which may provide such amounts biweekly, weekly, monthly and the like may also be employed. A dosing period of at least one to two weeks are required to achieve minimal benefit.

EXAMPLE 1

A pravastatin formulation in the form of tablets having the following composition was prepared as described below.

| Ingredient | Parts by Weight |
| --- | --- |
| Pravastatin | 7 |
| Lactose | 67 |
| Microcrystalline cellulose | 20 |
| Croscarmellose sodium | 2 |
| Magnesium stearate | 1 |
| Magnesium oxide | 3 |

Pravastatin, magnesium oxide and a fraction (30%) of the lactose were mixed together for 2 to 10 minutes employing a suitable mixer. The resulting mixture was passed through a 12 to 40 mesh size screen. Microcrystalline cellulose, croscarmellose sodium and the remaining lactose were added and the mixture was mixed for 2 to 10 minutes. Thereafter, magnesium stearate was added and mixing was continued for 1 to 3 minutes.

The resulting homogeneous mixture was then compressed into tablets each containing 5 mg or 10 mg pravastatin which may be used alone in preventing hypertension in normotensives with insulin resistance.

A captopril formulation suitable for oral administration together with pravastatin is prepared as described below.

1000 tablets each containing 100 mg of 1-[(2S)-3-mercapto-2-methylpropionyl]-L-proline were produced from the following ingredients.

| 1-[(2S)-3-Mercapto-2-methylpropionyl]-L-proline (captopril) | 7 g |
| --- | --- |
| Corn starch | 50 g |

| -continued | |
|---|---|
| Gelatin | 7.5 g |
| Avicel (microcrystalline cellulose) | 25 g |
| Magnesium stearate | 2.5 g |

The captopril and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 7 mg of active ingredient.

The pravastatin tablets and captopril tablets may be administered as a combination in accordance with the teachings of the present invention to prevent hypertension in normotensives with insulin resistance. In addition, the pravastatin and captopril tablets may be ground up into powders and used together in a single capsule.

EXAMPLE 2

Pravastatin tablets are prepared employing conventional pharmaceutical techniques containing 20 mg pravastatin and inert ingredients employed in lovastatin tablets, namely cellulose, color, lactose, magnesium stearate and starch and butylated hydroxyanisole as a preservative as described in the 1990 PDR.

The prevastatin tablets may be employed alone or in combination with enalapril tablets containing 7 mg enalapril and inactive ingredients as described in the 1990 PDR, in separate or combined dosage forms to prevent hypertension in accordance with the present invention.

EXAMPLE 3

Tablets containing 500 mg clofibrate by itself or in combination with 5 mg enalapril and inactive ingredients as described in the 1990 PDR, may be employed in separate dosage forms or combined in a single capsule form to prevent hypertension in accordance with the present invention.

EXAMPLES 4 to 6

Ciprofibrate, benzafibrate, clinofibrate alone or in combination with captopril, ceranapril or fosinopril may also be prepared in a manner described hereinbefore in Example 1 to 3 for use in preventing hypertnesion.

EXAMPLE 7

Fenofibrate tablets containing 250 mg fenofibrate are prepared employing conventional procedures containing the following additional ingredients: corn starch, ethyl cellulose, glycerin, hydroxypropyl cellulose, hydroxypropylmethyl cellulose 2910, iron oxide, lactose, magnesium stearate, microcrystalline cellulose, polysorbate 80, talc and titanium dioxide.

The fenofibrate tablets are employed alone or with 5 mg lisinopril tablets for preventing hypertension.

EXAMPLE 8

Tablets of the following compositions are prepared as described below.

| Ingredient | Weight (mg) |
|---|---|
| (E,E)-[difluoro[hydroxy(4,8,12-trimethyl-3,7,11-tridecatrienyl)- | 100 mg |

| -continued | |
|---|---|
| Ingredient | Weight (mg) |
| phosphinyl]methyl]phosphonic acid tripotassium salt (squalene synthetase inhibitor prepared as described by Biller et al. supra) | |
| Avicel | 112.5 mg |
| Lactose | 113 mg |
| Cornstarch | 17.5 mg |
| Stearic Acid | 7 mg |
| | 350 mg |

The tablets are prepared from sufficient bulk quantities by slugging the squalene synthetase inhibitor Avicel, and a portion of the stearic acid. The slugs are ground and passed through a #2 screen and then mixed with the lactose, cornstarch, and the remainder of stearic acid. The mixture is compressed into 350 mg capsule shaped tablets in a tablet press. The tablets are scored for dividing in half.

The squalene synthetase inhibitor tablets may be administered alone as in accordance with the teachings of the present invention or together with 5 mg captopril tablets to prevent hypertension.

EXAMPLES 9 and 10

Lovastatin tablets are prepared employing conventional pharmaceutical techniques containing 20 mg lovastatin, cellulose, color, lactose, magnesium stearate and starch and butylated hydroxyanisole as a preservative as described in the 1990 PDR.

The lovastatin tablets may be employed alone or in combination with the fenofibrate tablets (described in Example 7) in separate or combined dosage forms to prevent hypertension in accordance with the present invention.

EXAMPLES 11 to 12

A formulation in the form of tablets having the following composition is prepared as described in Example 1.

| Ingredient | Weight (mg) |
|---|---|
| (E,E,E)-[difluoro[hydroxy(4,8,12-trimethyl-1,3,7,11-tridecatetraenyl)phosphinyl]methyl]-phosphonic acid tripotassium salt (squalene synthetase inhibitor prepared as described by Biller et al. supra) | 100 mg |
| Cornstarch | 50 mg |
| Gelatin | 7.5 mg |
| Avicel (microcrystalline cellulose) | 25 mg |
| Magnesium stearate | 2.5 mg |
| | 185 mg |

The above formulations alone or with captopril tablets, or ceranapril tablets may be employed in separate dosage forms or combined in a single capsule form to prevent hypertension in accordance with the present invention.

EXAMPLE 13

Probucol tablets containing 250 mg probucol are prepared employing conventional procedures containing the following additional ingredients as set out in the 1990 PDR: corn starch, ethyl cellulose, glycerin, hydroxypropyl cellulose, hydroxypropylmethyl cellulose 2910, iron oxide, lactose, magnesium stearate, microcrystalline cellulose, polysorbate 80, talc and titanium dioxide.

The ACE inhibitor formulations described in the previous examples may be employed with probucol tablets as a combination in accordance with the teachings of the present invention to prevent hypertension. In addition, any or all of the above drugs and probucol tablets may be ground up into powders and used together in a single capsule.

EXAMPLE 14

Capsules containing 300 mg gemfibrozil are prepared employing conventional pharmaceutical techniques containing the following additional ingredients as described in the 1990 PDR: polysorbate 80 NF, starch NF and silica gel.

The gemfibrozil capsules may be administered alone or as a combination with any of the ACE inhibitor tablets and may be ground into a powder and used in a single capsule containing gemfibrozil and ACE inhibitor to prevent hypertension.

EXAMPLE 15

ACE inhibitor tablets as described above may be employed in combination with cholestyramine resin containing 4 g cholestyramine, acacia, citric acid, color, flavor, polysorbate 80, propylene glycol alginate and sucrose as described in the 1990 PDR to prevent hypertension in accordance with the present invention.

EXAMPLE 16

ACE inhibitor tablets, described above may be employed in combination with nicotinic acid, colestipol, dextrothyroxine or other serum cholesterol lowering agent in accordance with the teaching of the present invention to prevent hypertension.

It will also be appreciated that any of the cholesterol lowering drugs may be employed alone or in combination with any of the ACE inhibitors disclosed herein in accordance with the present invention.

What is claimed is:

1. A method for preventing or reducing the risk of hypertension in a normotensive mammalian species having insulin resistance, which comprises administering to a mammalian species in need of such treatment an effective amount of a cholesterol lowering drug which is an HMG CoA reductase inhibitor.

2. The method as defined in claim 1 wherein said inhibitor of the enzyme HMG CoA reductase is mevastatin, lovastatin, pravastatin or velosatin.

3. A method for preventing or reducing the risk of hypertension in a normotensive mammalian species having insulin resistance, which comprises administering to a normotensive mammalian species in need of such treatment a combination of an effective amount of cholesterol lowering drug which is an HMG CoA reductase inhibitor and an effective amount of an angiotensin converting enzyme inhibitor.

4. The method as defined in claim 3 wherein the ACE inhibitor is administered in an amount below that required to cause hemodynamic effects.

5. The method as defined in claim 3 wherein the angiotensin converting enzyme inhibitior is a substituted proline derivative.

6. The method as defined in claim 3 wherein said angiotensin converting enzyme inhibitor includes a mercapto moiety and is a substituted proline derivative.

7. The method as defined in claim 3 wherein said angiotensin converting enzyme inhibitor is captropril or fosinopril.

8. The method as defined in claim 3 wherein said angiotensin converting enzyme inhibitor is captopril, zofenopril, enalapril, cernapril, fosinopril, lisinopril or fentiapril.

9. The method as defined in claim 3 wherein the angiotensin converting enzyme inhibitor is a phosphonate substituted amino or imino acid or salt thereof, a proline derivative, a substituted proline derivative, a mercaptoacyl derivative of a substituted proline, a carboxyalkyl dipeptide derivative, a phonphinylalkanoly derivative or a phosphonamidate derivative.

10. The method as defined in claim 9 wherein said angiotensin converting enzyme inhibitor is a carboxyalkyl dipeptide derivative.

11. The method as defined in claim 3 wherein said angiotensin converting enzyme inhibitor is a phosphinylalkanoyl proline derivative, a phosphoramidate derivative, or a phosphonate substituted amino or imino acid or salt thereof.

12. The method as defined in claim 3 wherein the cholesterol lowering drug is present in a weight ratio to said ACE inhibitor of the of within the range of from about 0.001:1 to 1000:1.

13. The method as defined in claim 3 wherein the cholesterol lowering drug is prevastatin.

14. The method as defined in claim 3 wherein said angiotensin converting enzyme inhibitor is administered in single or divided doses of from about 0.1 to about 500 mg/one to four times daily.

15. The method as defined in claim 3 wherein the cholesterol lowering drug is pravastatin and the ACE inhibitor is captopril, fosinopril or ceranapril.

* * * * *

UNITED STATES PATENT AND TRADEMARK OFFICE
CERTIFICATE OF CORRECTION

PATENT NO. : 5,298,497
DATED : March 29, 1994
INVENTOR(S) : Werner Tschollar et al It is certified that error appears in the above-identified patent and that said Letters Patent is hereby corrected as shown below:

COLUMN 20
In Claim 9, line 28, please change "phonphinylalkanoly" to --phosphinylalkanoyl proline--.

Signed and Sealed this

Fifteenth Day of November, 1994

Attest:

BRUCE LEHMAN

Attesting Officer

Commissioner of Patents and Trademarks